United States Patent [19]

Victor

[11] Patent Number: 4,520,213
[45] Date of Patent: May 28, 1985

[54] METHOD FOR SOLVENT RECOVERY IN SOLVENT SEPARATION OF ETHANOL FROM WATER

[75] Inventor: John G. Victor, Indian Head Park, Ill.

[73] Assignee: Institute of Gas Technology, Chicago, Ill.

[21] Appl. No.: 513,922

[22] Filed: Jul. 14, 1983

Related U.S. Application Data

[63] Continuation-in-part of Ser. No. 374,402, May 3, 1982.

[51] Int. Cl.$^3$ ............... C07C 29/76; C07C 31/08; C07C 29/86; C07C 7/144
[52] U.S. Cl. ............... 568/913; 568/916; 568/918; 585/818
[58] Field of Search ............ 568/913, 916, 918; 585/818

[56] References Cited

U.S. PATENT DOCUMENTS

| | | | |
|---|---|---|---|
| 2,960,462 | 11/1960 | Lee et al. | 585/818 |
| 3,035,060 | 5/1962 | Binning et al. | 568/913 |
| 3,062,905 | 11/1962 | Jennings et al. | 568/913 |
| 3,244,763 | 4/1966 | Cahn | 585/818 |
| 3,950,247 | 4/1976 | Chiang et al. | 568/913 |
| 4,035,291 | 7/1977 | Chiang et al. | 568/913 |
| 4,349,415 | 9/1982 | DeFilippi et al. | 560/261 |

FOREIGN PATENT DOCUMENTS

| | | | |
|---|---|---|---|
| 2627629 | 12/1977 | Fed. Rep. of Germany | 585/818 |
| 856371 | 12/1960 | United Kingdom | 568/913 |
| 0827474 | 5/1981 | U.S.S.R. | 568/913 |

OTHER PUBLICATIONS

Binning et al., "The Refining Engineer", Jun. 1958, pp. C–14 and C–15.

Primary Examiner—J. E. Evans
Attorney, Agent, or Firm—Allegretti, Newitt, Witcoff & McAndrews, Ltd.

[57] ABSTRACT

A process for the separation of ethanol from water using solvent extraction at elevated pressures is disclosed. Separation is effected by contacting aqueous ethanol with either propylene (propene), allene (propadiene), methyl acetylene (propyne), or methyl allene (1,2-butadiene). This produces two liquid layers which separate because of the difference in their densities, and are easily drawn off as separate streams. The solvent is recovered by reverse osmosis means in a liquid state. The ethanol and water remain in a liquid state and are substantially recovered.

5 Claims, 1 Drawing Figure

METHOD FOR SOLVENT RECOVERY IN SOLVENT SEPARATION OF ETHANOL FROM WATER

REFERENCE TO RELATED APPLICATION

This is a continuation-in-part application of copending application, Ser. No. 374,402, filed on May 3, 1982.

BACKGROUND OF THE INVENTION

This invention relates to a solvent extraction process useful for the separation of ethanol from water, a principal benefit of which is a low energy requirement.

Certain specific processes which use solvent extraction to separate different organic liquids by selective solvent action are well-known in the art. For example, ethylene is used as a solvent to separate water-organic mixtures in J. C. Elgin and J. J. Weinstock, "Phase Equilibrium At Elevated Pressures In Ternary Systems Of Ethylene And Water With Organic Liquids", J. Chem. and Engr. Data, Vol. 4, No. 1, January, 1959, pp. 3–12. However, ethylene has not been found to be an effective solvent for use in solvent extraction of such mixtures due to the low distribution coefficient of ethylene in water and organic liquid mixtures.

At present, solvents are used to separate ethanol from water only when very high concentrations (90–95% ethanol, by volume) of ethanol and water are involved, because ethanol forms an azeotrope with water at a concentration of about 95% ethanol, by volume, and distillation cannot increase the concentration of ethanol beyond this value. The use of benzene and ethyl ether in the extraction of absolute alcohol from an alcohol-water azeotrope is disclosed in D. F. Othmer and T. O. Wentworth, "Absolute Alcohol—An Economical Method For Its Manufacture", in Industrial and Engineering Chemistry, December, 1940, pp. 1588–1593.

Mann, U.S. Pat. No. 1,524,192 discloses the extraction of a high molecular weight alcohol, such as secondary butyl alcohol, from an aqueous solution, through the utilization of a hydrocarbon oil having a high initial boiling point, preferably above 325° F., as the solvent. Distillation is used to obtain the final dehydrated alcohol product.

In Carney, U.S. Pat. No. 2,048,178, a process for dehydrating organic compounds, such as secondary butyl alcohol, is disclosed. Olefin and parrafin hydrocarbons, such as pentane, isopentene and butane, which are substantially insoluble in water and soluble in the organic compound, are used as solvents. Carney utilizes steam in order to maintain process temperatures and to separate the solvent and organic compounds. This results in high energy costs. In addition, Carney fails to disclose the separation of ethanol from an aqueous medium through the utilization of his process and solvents.

In Van Dijck, et al., U.S. Pat. No. 2,081,721, a process for separating a liquid mixture, containing one or more organic polar compounds, into two components or two groups of components, by solvent extraction, is disclosed. The process includes a washing step, in which the separated extract or solvent-rich phase is washed with a liquid stream of a nearly pure component. This process, like the process in Carney, is intended for use in the separation of water from an alcohol higher than ethanol, e.g., propyl and butyl alcohols, by using a hydrocarbon, such as pentane, as the extracting agent.

The feasibility of using solvent extraction as a substitute for distillation in alcohol separation and concentration was studied in J. W. Roddy, "Distribution Of Ethanol-Water Mixtures To Organic Liquids", Ind. Eng. Chem. Process Des. Dev., Vol. 20, No. 1, 1981. All of the solvents studied were liquids at ambient temperature and atmospheric pressure.

The prior art separation processes heretofore developed for the separation of ethanol and water have process temperatures or solvent requirements which require large energy inputs and thus high energy costs. The present invention obviates the need for large energy inputs through the use of allene, methyl allene, propylene and methyl acetylene as solvents in a solvent extraction process.

By using these solvents, which are in the vapor state at ambient temperature and pressure, the energy required for their recovery, by reverse osmosis, is minimized. The recovery of the solvents is achieved through the use of a polymer membrane composed of a hydrophobic polymer which preferentially separates hydrogen-bonding from non-hydrogen-bonding molecules. The pressure drop across the membrane provides the driving force to achieve the separation.

SUMMARY OF THE INVENTION

It is an object of the present invention to provide a process for the separation of ethanol from water which is a less energy-intensive method than distillation.

A further object of the present invention is to provide a process to separate a liquid mixture of ethanol and water into at least two liquid streams or groups of liquid streams, one with a higher concentration of ethanol than the original mixture, the other with a lower concentration of ethanol.

It is a further object of the present invention to provide a process to separate ethanol from water in which the solvent may be substantially recovered by reverse osmosis, thereby minimizing energy requirements.

Another object of the present invention relates to a process for the separation of ethanol from water through the utilization of solvent extraction in which propylene (propene), allene (propadiene), methyl acetylene (propyne) or methyl allene (1, 2 - butadiene) may be used as the liquid solvent.

In a principal aspect, the present invention relates to a process for the separation of ethanol from water through the utilization of solvent extraction with propylene (propene) being used as the liquid solvent. The process is performed by combining a liquid mixture containing ethanol and water and propylene. This produces two layers or phases, one enriched in ethanol and the other in water. The resulting layers are then separated. The solvent is substantially recovered from the layers through reverse osmosis. A hydrophobic polymer membrane is utilized which preferentially separates hydrogen-bonding molecules, such as ethanol and water, from non-hydrogen-bonding molecules, such as propylene. The pressure drop across the membrane provides the driving force for the separation. In this fashion, energy costs are minimized.

These and other objects, advantages and features of the invention will be set forth in the detailed description which follows.

BRIEF DESCRIPTION OF THE DRAWING

In the detailed description which follows, reference will be made to the drawing comprising of the following figure.

DETAILED DESCRIPTION OF THE PREFERRED EMBODIMENT

Figure 1:
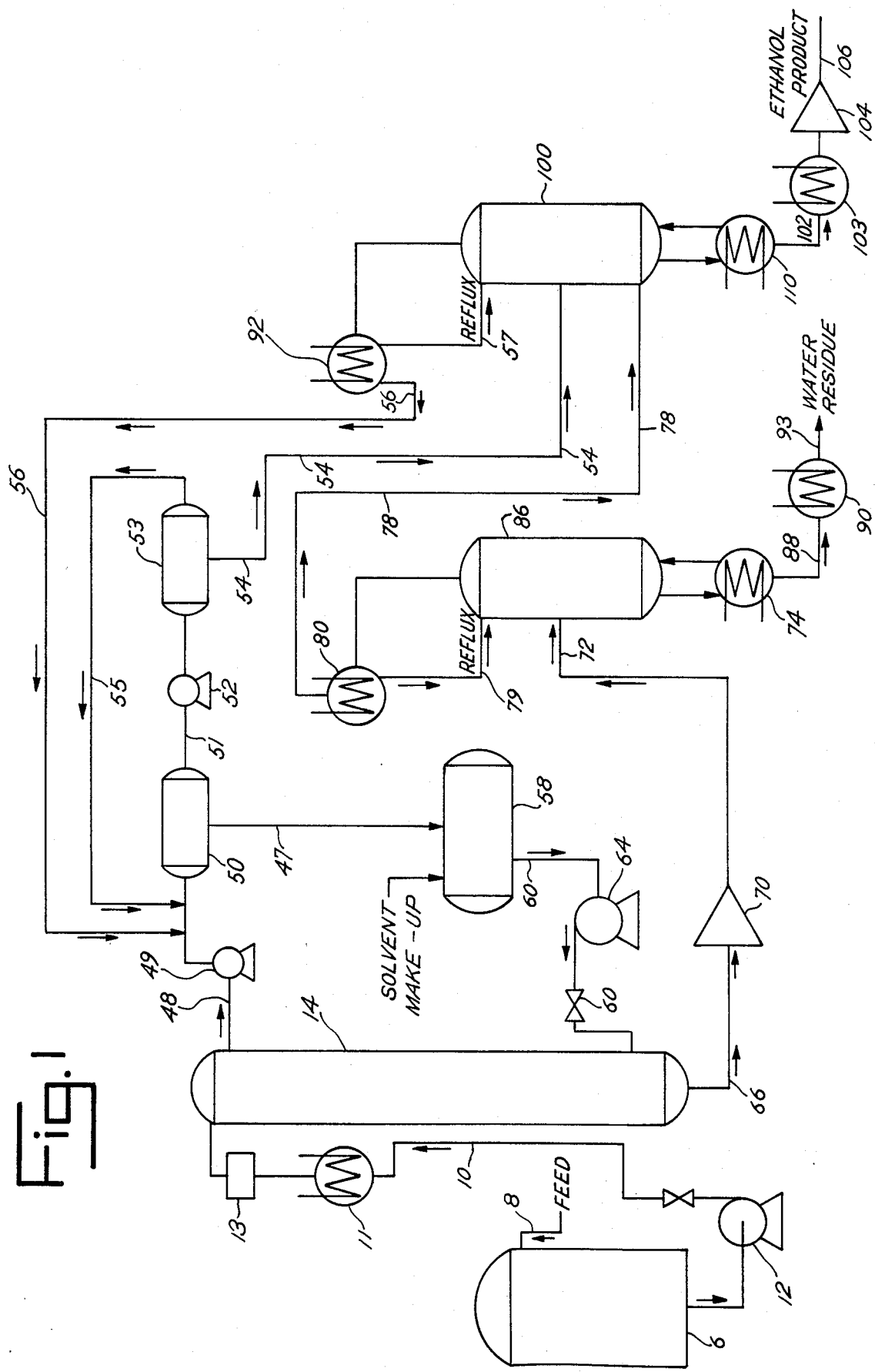
FIG. 1 is a schematic flow diagram illustrating a preferred embodiment of the disclosed process.

In general terms, the present invention relates to a means for separating ethanol from water by solvent extraction. A liquid mixture containing at least ethanol and water is contacted with a liquid solvent, which is, preferably, propylene (propene), but may also be allene (propadiene), methyl acetylene (propyne) or methyl allene (1, 2 - butadiene), to produce a liquid mixture containing separate layers. The top layer contains solvent which must be recovered. The bottom layer will contain a small amount of solvent which also must be recovered. Solvent recovery and the production of an ethanol stream having an enriched ethanol content is effected by reverse osmosis means utilizing hydrophobic polymer membranes which preferentially separate hydrogen-bonding molecules, such as ethanol and water, from non-hydrogen-bonding molecules, such as the above solvents. The pressure drop across the membrane provides the driving force for the separation.

A more detailed explanation of the process is set forth with reference to FIG. 1, which is a schematic flow diagram of a preferred embodiment of the process.

In a preferred embodiment of the present invention, as in FIG. 1, a mixture containing ethanol and water, as received from feed line 8, is stored in an ethanol storage vessel 6.

The mixture is pumped, through line 10, by a pump 12, from vessel 6 through a heat exchanger 11 which increases its temperature, through a heater 13 which further increases the temperature of the mixture and into a solvent extractor separation vessel 14. Solvent, which is, preferably, propylene, but may also be allene, methyl acetylene or methyl allene, is pumped, through line 60 by pump 64, into the solvent extractor 14 from a solvent storage vessel 58.

In the solvent extractor 14, the solvent and the aqueous ethanol are mixed to produce a lighter, solvent-rich, ethanol enriched layer, and a heavier, water-rich, ethanol-depleted layer. The two layers are drawn off separately from solvent extractor 14, via lines 48 and 66, respectively. The separation of the ethanol from water is achieved by:

(1) The ability of the solvent to dissolve some ethanol, but little, if any, water;

(2) The amount of contact, or interfacial surface area, between solvent and the ethanol-water mixture; and (3) The difference in the densities between light and heavy layers, which allows them to separate.

The heavier, water-rich layer and especially the lighter, ethanol-enriched layer each contain some solvent which should be recovered and recycled. Typically, the recovery of solvent from ethanol and the production of an ethanol-enriched product is conveniently carried out by reverse osmosis. Upon leaving the solvent extractor 14, via line 48, the lighter, ethanol-enriched stream is pumped by pump 49, which increases the pressure of the stream to approximately 600 pounds per square inch. The stream then enters hydrophobic membrane separator 50 wherein the reverse osmosis separation step takes place. In separator 50, the stream contacts hydrophobic-type polymer membranes, which may be polypropylene membranes, which are selective for propylene. The membranes preferentially separate the solvent from the solvent-ethanol mixture, thereby reducing the ethanol content of the solvent by a factor of approximately two hundred. The driving force for the separation is a pressure drop of approximately 200 pounds per square inch across membranes. No large expenditure of energy is required to effect the separation. The recovered propylene is passed via line 47 to solvent storage vessel 58.

The residual ethanol solvent stream leaves separator 50 via line 51, and is pumped by pump 52 to a pressure of approximately 1200 pounds per square inch. The stream then enters hydrophilic membrane separator 53, wherein a more concentrated ethanol stream is produced. In separator 53, the stream contacts hydrophilic-type polymer membranes, which may be cellulose acetate membranes, which are selective for ethanol. The membranes preferentially concentrate ethanol from residual solvent-ethanol mixture, thereby increasing the ethanol content by a factor of approximately six. Again, the driving force for the concentration is a pressure drop of approximately 800 pounds per square inch across the membranes. The residual solvent is reduced in pressure and returned via line 55 to membrane separator 50.

On the low pressure side of the membranes in separator 53, the resulting ethanol stream is concentrated to the point where distillation of any remaining volatile solvent is feasible. The distillation is conveniently carried out in a pressurized distillation column 100. The concentrated ethanol passes, via line 54, into the distillation column 100. The vapor containing solvent issues from the top of the column 100, into a condenser 92. Some condensed solvent may be returned to the distillation column 100, as reflux via line 57. Within the distillation column 100, the feed stream descends and contacts solvent and ethanol vapor. This vapor, introduced to the base of the column 100 and effervescing upward, acts to vaporize the liquid solvent. It exits from the top of column 100.

The condenser 92 removes enough heat to transform the saturated vapor to a liquid. The condensed solvent is pumped to a higher pressure and recycled, via line 56, to membrane separator 50. The ethanol product stream flows out of the bottom of the distillation column 100 into reboiler 110, wherein heat is added to the liquid stream to partially vaporize it. The vapor is returned to column 100. The resulting liquid flows out of the bottom of the reboiler 110 via line 102, and passes through a cooler 103 and a turbine 104, which lowers the pressure of the ethanol. The resulting ethanol product issues from the process via line 106.

Solvent recovery from the water-rich layer preferably proceeds by distillation. Upon leaving the solvent extractor 14, via line 66, the water-rich stream passes through a turbine 70, which lowers the pressure of the stream. The stream then passes via line 72 into distillation column 86. The solvent vapor issues from the top of the column 86, into a condenser 80. The condensed solvent may be returned to the distillation column 86, as reflux via line 79. The condenser 80 removes enough heat to transform the saturated solvent vapor into a saturated liquid. The uncondensed solvent is compressed and then returned, via line 78, to distillation column 100 for further purification.

The water stream flows out of the bottom of the distillation column 86 into reboiler 74, wherein heat is added to the stream to partially vaporize it. The vapor is returned to column 86. The resulting liquid flows out of the bottom of reboiler 74, via line 88, and passes through a cooler 90, which lowers the temperature of the water. The water is then removed from the process via line 93.

The present invention can be better understood with reference to the following example:

ILLUSTRATIVE EXAMPLE I

With reference to FIG. 1, the following descriptive flow rates are proportional to flow rates which could be utilized in the process, and are based upon experimental tests and evaluations.

181,400 lbs/hr. of a mixture, containing 7.1% by weight ethanol and 92.9% by weight water at a temperature of 20° C. and a pressure of 1 atm. (absolute), is pumped through line 10, to a heater exchanger 11 which increases its temperature to 45° C. The mixture is further heated to 60° C. in a heater 13, and then enters a solvent extractor separation vessel 14. Vessel 14 is maintained at a temperature of 60° C. and a pressure of 375 psia. 1,081,700 lbs/hr. of propylene, at a temperature of 60° C. and a pressure of 372 psia. are then introduced into the solvent extractor 14, via line 60, to provide contact with the ethanol and water.

The solvent extractor 14 should be of a height, for this example, sufficient to provide approximately 150 equilibrium stages. The height of an equilibrium stage will vary depending upon the type of packing, or internal trays, inside the extractor. Plastic rings are a typical type of packing. it will also vary to a certain extent with the velocity of propylene flowing through it. In any event, this velocity of propylene must be less than that which would cause the extractor to "flood", that is, entrain water with the propylene leaving the top.

In the continuous counter-current solvent extractor 14 of this example (other types may also be utilized), the aqueous ethanol descends as small droplets through a rising liquid stream of propylene. Approximately 150 equilibrium stages allow the production of a substantially water-free, light, ethanol-rich layer containing 1.4% ethanol and 98.6% by weight propylene. The heavier, water-rich layer contains only trace amounts of ethanol and propylene. The light layer is removed at a rate of 1,094,400 lbs/hr., the heavy layer, at 168,700 lbs/hr. The 168,700 lbs/hr. of water and ethanol, of which 168,500 lbs/hr. is water, leaves the solvent extraction vessel 14 and has its pressure reduced to approximately 14.7 psia. The water and ethanol, still at approximately 60° C., then enter a distillation column 86 which may, for example, be a flash vaporizer. Trace amounts of propylene, ethanol and water vapor issue from the top of the distillation column 86 and are cooled and substantially condensed in a condenser 80. The condensed liquid leaving condenser 80 consists of ethanol and water and may be returned to the distillation column 86 or alternatively to the feed tank 6. The approximately 168,500 lbs/hr. of water leaves the bottom of the distillation column 86 and is cooled from 60° C. to 35° C. in cooler 90 and is discharged from the process.

The propylene-ethanol stream flows, via line 48, through a pump 49 which increases its pressure to approximately 600 psia. The stream then enters a hydrophobic membrane separator 50. The membranes may be polypropylene film in a hollow fiber configuration. A pressure drop of 200 psi. across the membranes causes propylene to permeate preferentially and to separate most of the propylene from the entering stream of ethanol and propylene. Approximately 1,081,700 lbs/hr. of purified propylene at 60° C. and 400 psia. are returned to the solvent storage vessel 58. The residual stream from membrane separator 50 leaves via line 51 at 60° C. and approximately 600 psia., containing approximately 10 weight percent ethanol. This stream is pumped by pump 52 to a pressure of approximately 1200 psia. and then enters a hydrophilic membrane separator 53. The membranes may be cellulose acetate film in a hollow fiber configuration. A pressure drop of 800 psi. across the membrane causes ethanol to permeate preferentially and to concentrate most of the ethanol from the entering stream of ethanol and propylene. Approximately 21,500 lbs/hr. of concentrated ethanol at 400 psia. and 60° C., consisting of approximately 60 weight percent ethanol are sent via line 54 to the distillation column 100 further ethanol purification. The residual stream from membrane separator 53 containing approximately 3 weight percent ethanol leaves via line 55 at a rate of 153,600 lbs/hr. and returns to the inlet of membrane separator 50.

The concentrated ethanol stream travels, via line 54, to distillation column 100 which is maintained at a pressure of 375 psia. Ethanol-free solvent vapor leaves at the top of column 100, and the liquid feed descends from the feed point enriched in ethanol and leaves at the bottom of the column 100.

The propylene present in the ethanol leaving the column 100 is removed by heating in the reboiler 110 and is returned to the column 100 as slightly superheated propylene vapor. The 12,880 lbs/hr. of ethanol product stream leaves the reboiler 110, via line 102, at 60° C., is cooled in cooler 103 to approximately 20° C. and then has its pressure reduced to 14.7 psia. by a pressure reducing device 104.

The 8,620 lbs/hr. of propylene vapor issuing from the distillation column 100 flows to a condenser 92, maintained at 375 psia. and 60° C., where sufficient heat is removed to condense the propylene vapor. The 8,620 lbs/hr. of liquid propylene are pumped to a pressure of 600 psia. and flow to the inlet of membrane separator 50.

The pressure at which the solvent extraction process of the present invention can be operated is the vapor pressure of the solvent at the temperature of extraction. Pressures less than 400 psia. are desirable from the standpoint of vessel design. Typical temperatures at which the solvent extraction can be operated are in a range of 20° C. up to the critical temperature of the solvent, with 60° C. to 80° C. being a desirable range between higher ethanol distribution coefficients and higher pressure. The reverse osmosis step operates in the hydrophobic membrane separator at a pressure of 600 psia. and a temperature from 20° C. to 80° C., with lower temperatures being preferred, resulting in a driving force of 200 psi. across the membranes. The hydrophilic membrane separator is operated at a pressure of about 1200 psia. and temperatures of 20° C.–80° C. to produce a driving force of about 800 psi. across the membranes. Typical temperatures at which the distillation step is performed are from 20° C. to 80° C., with 20° C., or ambient temperature, being preferred. Typical pressures at which the distillation step is performed correspond to the vapor pressure of the solvent at the temperature of the distillation, typically around 375 psia. The ratio of solvent to liquid contacted in the extraction step is a function of the amount of alcohol contained in the liquid mixture and the degree of separation desired and is readily ascertainable by one skilled in the art. Typical ratios of the amount of solvent used to the amount of liquid mixture used, on a volume basis, range from 8 to 11, depending on the solvent, with 11 being preferred for greater ethanol recovery.

The process of the present invention can produce alcohol of approximately 100% by weight purity in a single, multi-stage extraction column. It also permits recovery of up to 100% by weight of the alcohol originally present in the liquid mixture fed to the column. A single operating stage can produce alcohol of approximately 100% by weight purity, but will permit recovery of only about 40% by weight of the alcohol originally present in the liquid mixture.

The solvents of the present invention, namely, propylene (propene), allene (propadiene), methyl acetylene (propyne) and methyl allene (1, 2 - butadiene), when used for solvent extraction, lead to a successful ethanol extraction, which has low energy requirements because the solvents are far easier to separate from ethanol than ethanol is from water.

It should be understood that the foregoing disclosure emphasizes certain specific embodiments of the invention and that all modifications or alternatives equivalent thereto are within the spirit or scope of the invention as set forth in the appended claims.

What is claimed is:

1. A process for the extraction of ethanol from a liquid mixture of ethanol and water comprising the steps of:
   (a) combining the liquid mixture with liquid solvent selected from a group consisting of propylene (propene), allene (propadiene), methyl acetylene (propyne), and methyl allene (1, 2 - butadiene) at a pressure of less than 400 psia and a temperature of from 20° to 80° C. to produce two layers, one layer being solvent and ethanol-rich, and the other being water-rich;
   (b) separating the ethanol and solvent-rich layer from the water-rich layer, thereby forming liquid streams, one stream being ethanol and solvent-rich, and the other being water-rich;
   (c) pressurizing the ethanol and solvent-rich stream;
   (d) separating the solvent from the ethanol by reverse osmosis means;
   (e) maintaining said solvent at a pressure such that said solvent remains in a liquid state;
   (f) recovering said solvent in a liquid state.

2. A process as in claim 1 wherein said liquid solvent is propylene (propene).

3. A process as in claim 1 wherein said liquid solvent is selected from a group consisting of allene (propadiene), methyl acetylene (propyne), and methyl allene (1, 2 - butadiene).

4. A process as in claim 1 wherein said reverse osmosis means comprises a first plurality of membranes for separating said solvent from said ethanol, said membranes being formed of a hydrophobic polymer and being selective for said solvent, and a second plurality of membranes for concentrating said ethanol, said membranes being formed of a hydrophilic polymer and being selective for ethanol.

5. A process as in claim 4 wherein said first plurality of membranes comprises polypropylene membranes and said second plurality of membranes comprises cellulose acetate membranes.

* * * * *